United States Patent [19]

Zenno et al.

[11] Patent Number: 5,578,476
[45] Date of Patent: Nov. 26, 1996

[54] FLAVIN REDUCTASE GENE

[75] Inventors: Shuhei Zenno, Yokohamashi; Satoshi Inouye; Kaoru Saigo, both of Tokyo, all of Japan

[73] Assignee: Chisso Corporation, Osaka, Japan

[21] Appl. No.: 518,223

[22] Filed: Aug. 23, 1995

Related U.S. Application Data

[63] Continuation of Ser. No. 250,855, May 27, 1994, abandoned.

[30] Foreign Application Priority Data

May 27, 1993 [JP] Japan .................................... 5-151076

[51] Int. Cl.⁶ .............................. C12N 9/02; C12N 15/63; C12N 1/21; C07H 21/04
[52] U.S. Cl. ................... 435/189; 435/320.1; 435/252.3; 536/23.2
[58] Field of Search ...................................... 435/189, 191, 435/320.1, 69.1, 252.3; 536/23.2

[56] References Cited

U.S. PATENT DOCUMENTS 4,234,681 11/1980 DeLuca-McElroy ........................ 435/8
5,484,723 1/1996 Zenno et al. ............................. 435/189

FOREIGN PATENT DOCUMENTS

547876A1 6/1993 European Pat. Off. ..

OTHER PUBLICATIONS

*American Society of Microbiology*, "Characterization of the Flavin Reductase Gene (fre) of *Escherichia coli* and . . . Enzyme", Giannis Spyrou et al., 1991, pp. 3673–3679.
*The Journal of Biological Chemistry*, vol. 262, No. 25, "NAD(P) H: Flavin Oxidoreductase of *Escherichia coli*", Marc Fontecave et al., 1987, pp. 12325–12331.
Schmidt, T. M. et al. (1989) "Bioluminescence of the insect pathogen Xenorhabdus luminescens" *Appl. Environ. Microbiol.* 55(10):2607–2612. Oct. 1989.

*Primary Examiner*—Robert A. Wax
*Assistant Examiner*—Kawai Lau
*Attorney, Agent, or Firm*—Leydig, Voit & Mayer

[57] ABSTRACT

Nucleic acids coding for the flavin reductase of a luminescent bacterium, *Xenorhabdus luminescens*, vectors comprising such nucleic acids, host cells into which such vectors have been introduced, recombinant methods for producing substantially purified recombinant flavin reductase, and recombinantly produced flavin reductase and equivalent proteins produced in accordance with such methods are provided.

16 Claims, 2 Drawing Sheets

FIG. I

FRE 1 (24mer):

N —Met Thr Thr Leu Ser Cys Lys Val—C
5' —ATG, ACA, ACC, TTA, AGC, TGT, AAA, GTG—3'

FRE 2 (24mer):

N —Gly Asp Ala Phe Ala Phe Ile ✱✱✱—C
3' —CCG, CTA, CGC, AAA, CGT, AAA, TAG, ACT—5'

S : Sal I
E : EcoR I
H : Hind III
B : Bal I
V : EcoR V
N : Nsp V
St: Sty I
Hp: Hpa I

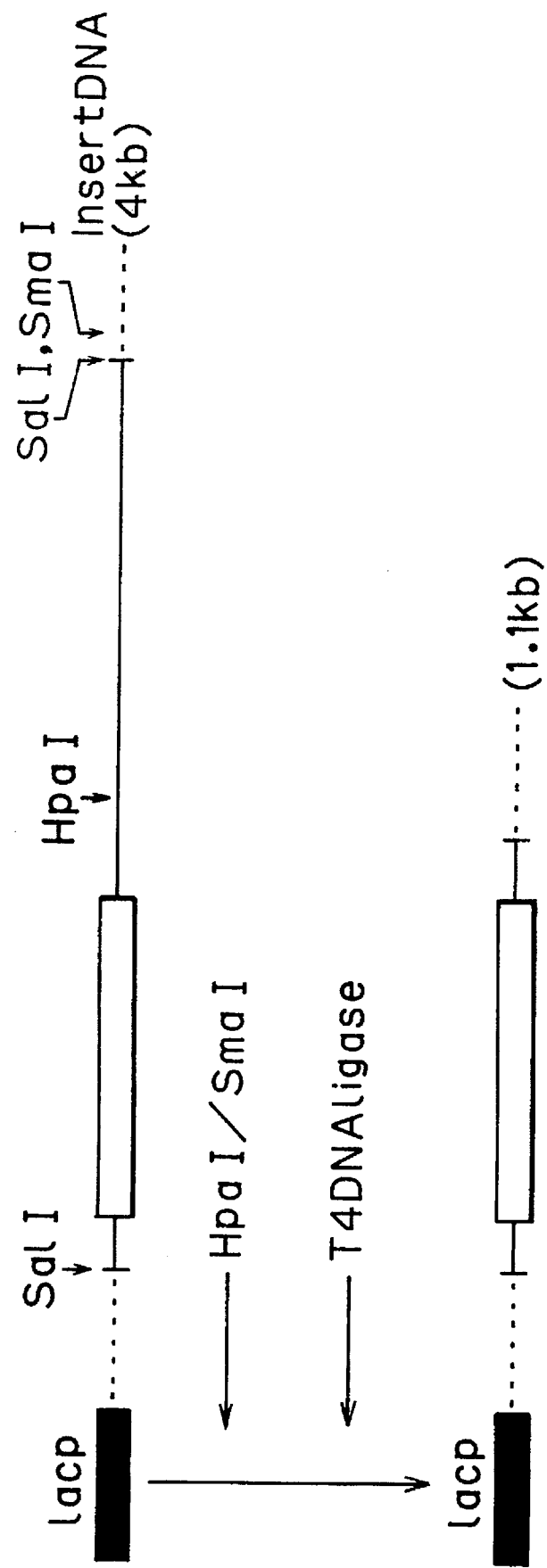

5,578,476

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 702 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..702

( x i ) SEQUENCE DESCRIPTION: SEQ ID NO:1:

```
ATG ACN ACN YTN NNN TGY AAR GTN ACN NNN GTN GAR GCN ATH ACN GAY      48
Met Thr Thr Leu Ser Cys Lys Val Thr Ser Val Glu Ala Ile Thr Asp
 1               5                  10                  15

ACN GTN TAY NGN GTN NGN YTN YTN CCN GAY NNN CCN TTY YTN TTY NGN       96
Thr Val Tyr Xaa Val Xaa Leu Leu Pro Asp Ser Pro Phe Leu Phe Xaa
                 20              25                  30

GCN GGN CAR TAY YTN ATG GTN GTN ATG GAY GAR NGN GAY AAR NGN CCN      144
Ala Gly Gln Tyr Leu Met Val Val Met Asp Glu Xaa Asp Lys Xaa Pro
             35              40                  45

TTY NNN ATG GCN NNN ACN CCN NNN GAR AAR GAR TTY ATH GAR YTN CAY      192
Phe Ser Met Ala Ser Thr Pro Ser Glu Lys Glu Phe Ile Glu Leu His
     50              55                  60

ATH GGN GCN NNN GAR YTN AAY YTN TAY GCN ATG GCN GTN ATG GAY NGN      240
Ile Gly Ala Ser Glu Leu Asn Leu Tyr Ala Met Ala Val Met Asp Xaa
 65              70                  75                      80

ATH YTN GAY CAR AAR GTN ATH AAY ATH GAY ATH CCN CAY GGN AAR GCN      288
Ile Leu Asp Gln Lys Val Ile Asn Ile Asp Ile Pro His Gly Lys Ala
                 85                  90                  95

TGG TTY NGN AAR NNN NNN GCN AAY CCN YTN YTN YTN ATH GCN GGN GGN      336
Trp Phe Xaa Lys Ser Ser Ala Asn Pro Leu Leu Leu Ile Ala Gly Gly
             100             105                 110

ACN GGN TTY NNN TAY ACN NGN NNN ATH YTN YTN ACN GCN YTN GAR GAR      384
Thr Gly Phe Ser Tyr Thr Xaa Ser Ile Leu Leu Thr Ala Leu Glu Glu
         115             120                 125

CAR CCN AAR NGN CAY ATH NNN ATG TAY TGG GGN GGN NGN GAR NNN CAR      432
Gln Pro Lys Xaa His Ile Ser Met Tyr Trp Gly Gly Xaa Glu Ser Gln
     130             135                 140

CAY YTN TAY GAY YTN GCN GAR YTN NGN YTN YTN ACN GAR NGN TAY CCN      480
His Leu Tyr Asp Leu Ala Glu Leu Xaa Leu Leu Thr Glu Xaa Tyr Pro
145                 150                 155                 160

AAY YTN AAR GTN ATH CCN GTN GTN GAR CAR NNN GAY AAY GGN TGG TGY      528
Asn Leu Lys Val Ile Pro Val Val Glu Gln Ser Asp Asn Gly Trp Cys
                 165                 170                 175

GGN NGN ACN GGN ACN GTN YTN AAR GCN GTN YTN GAR GAY TTY GGN NNN      576
Gly Xaa Thr Gly Thr Val Leu Lys Ala Val Leu Glu Asp Phe Gly Ser
             180                 185                 190

YTN GCN AAY TAY GAY ATH TAY ATH GCN GGN NGN TTY GAR ATG GCN AAR      624
Leu Ala Asn Tyr Asp Ile Tyr Ile Ala Gly Xaa Phe Glu Met Ala Lys
         195                 200                 205

ATH GCN NGN GAR NGN TTY TGY NNN GAR NGN GAY GCN NNN GCN GAY NNN      672
Ile Ala Xaa Glu Xaa Phe Cys Ser Glu Xaa Asp Ala Ser Ala Asp Ser
210                 215                 220

ATG TAY GGN GAY GCN TTY GAR TTY ATH TRR                              702
Met Tyr Gly Asp Ala Phe Glu Phe Ile
225                 230
```

( 2 ) INFORMATION FOR SEQ ID NO:2:

( i ) SEQUENCE CHARACTERISTICS:
        ( A ) LENGTH: 702 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..702

( x i ) SEQUENCE DESCRIPTION: SEQ ID NO:2:

```
ATG ACN ACN YTN NNN TGY AAR GTN ACN NNN GTN GAR GCN ATH ACN GAY      48
Met Thr Thr Leu Ser Cys Lys Val Thr Ser Val Glu Ala Ile Thr Asp
```

| | 1 | | | 5 | | | | | 10 | | | | | 15 | | |
|---|---|---|---|---|---|---|---|---|---|---|---|---|---|---|---|---|
| | ACN Thr | GTN Val | TAY Tyr | NGN Arg 20 | GTN Val | NGN Arg | YTN Leu | YTN Leu | CCN Pro 25 | GAY Asp | NNN Ser | CCN Pro | TTY Phe | YTN Leu 30 | TTY Phe | NGN Arg | 96 |
| | GCN Ala | GGN Gly | CAR Gln 35 | TAY Tyr | YTN Leu | ATG Met | GTN Val | GTN Val 40 | ATG Met | GAY Asp | GAR Glu | NGN Arg | GAY Asp 45 | AAR Lys | NGN Arg | CCN Pro | 144 |
| | TTY Phe | NNN Ser 50 | ATG Met | GCN Ala | NNN Ser | ACN Thr | CCN Pro 55 | NNN Ser | GAR Glu | AAR Lys | GAR Glu | TTY Phe 60 | ATH Ile | GAR Glu | YTN Leu | CAY His | 192 |
| | ATH Ile 65 | GGN Gly | GCN Ala | NNN Ser | GAR Glu | YTN Leu 70 | AAY Asn | YTN Leu | TAY Tyr | GCN Ala | ATG Met 75 | GCN Ala | GTN Val | ATG Met | GAY Asp | NGN Arg 80 | 240 |
| | ATH Ile | YTN Leu | GAY Asp | CAR Gln | AAR Lys 85 | GTN Val | ATH Ile | AAY Asn | ATH Ile | GAY Asp 90 | ATH Ile | CCN Pro | CAY His | GGN Gly | AAR Lys 95 | GCN Ala | 288 |
| | TGG Trp | TTY Phe | NGN Arg | AAR Lys 100 | NNN Ser | NNN Ser | GCN Ala | AAY Asn | CCN Pro 105 | YTN Leu | YTN Leu | YTN Leu | ATH Ile | GCN Ala 110 | GGN Gly | GGN Gly | 336 |
| | ACN Thr | GGN Gly | TTY Phe 115 | NNN Ser | TAY Tyr | ACN Thr | NGN Arg | NNN Ser 120 | ATH Ile | YTN Leu | YTN Leu | ACN Thr | GCN Ala 125 | YTN Leu | GAR Glu | GAR Glu | 384 |
| | CAR Gln | CCN Pro 130 | AAR Lys | NGN Arg | CAY His | ATH Ile 135 | NNN Ser | ATG Met | TAY Tyr | TGG Trp | GGN Gly 140 | GGN Gly | NGN Arg | GAR Glu | NNN Ser | CAR Gln | 432 |
| | CAY His 145 | YTN Leu | TAY Tyr | GAY Asp | YTN Leu 150 | GCN Ala | GAR Glu | YTN Leu | NGN Arg | YTN Leu 155 | YTN Leu | ACN Thr | GAR Glu | NGN Arg | TAY Tyr | CCN Pro 160 | 480 |
| | AAY Asn | YTN Leu | AAR Lys | GTN Val | ATH Ile 165 | CCN Pro | GTN Val | GTN Val | GAR Glu | CAR Gln 170 | NNN Ser | GAY Asp | AAY Asn | GGN Gly | TGG Trp 175 | TGY Cys | 528 |
| | GGN Gly | NGN Arg | ACN Thr | GGN Gly 180 | ACN Thr | GTN Val | YTN Leu | AAR Lys | GCN Ala 185 | GTN Val | YTN Leu | GAR Glu | GAY Asp | TTY Phe 190 | GGN Gly | NNN Ser | 576 |
| | YTN Leu | GCN Ala | AAY Asn 195 | TAY Tyr | GAY Asp | ATH Ile | TAY Tyr | ATH Ile 200 | GCN Ala | GGN Gly | NGN Arg | TTY Phe | GAR Glu 205 | ATG Met | GCN Ala | AAR Lys | 624 |
| | ATH Ile | GCN Ala 210 | NGN Arg | GAR Glu | NGN Arg | TTY Phe | TGY Cys 215 | NNN Ser | GAR Glu | NGN Arg | GAY Asp | GCN Ala 220 | NNN Ser | GCN Ala | GAY Asp | NNN Ser | 672 |
| | ATG Met 225 | TAY Tyr | GGN Gly | GAY Asp | GCN Ala | TTY Phe 230 | GAR Glu | TTY Phe | ATH Ile | TRR | | | | | | | 702 |

( 2 ) INFORMATION FOR SEQ ID NO:3:

( i ) SEQUENCE CHARACTERISTICS:
        ( A ) LENGTH: 702 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..702

( x i ) SEQUENCE DESCRIPTION: SEQ ID NO:3:

| ATG Met 1 | ACA Thr | ACA Thr | CTG Leu | AGC Ser 5 | TGT Cys | AAA Lys | GTA Val | ACC Thr | TCT Ser 10 | GTA Val | GAG Glu | GCT Ala | ATT Ile | ACT Thr 15 | GAT Asp | 48 |
|---|---|---|---|---|---|---|---|---|---|---|---|---|---|---|---|---|
| ACG Thr | GTT Val | TAT Tyr | CGG Arg | GTA Val | CGG Arg | TTG Leu | CTT Leu | CCC Pro | GAT Asp | TCT Ser | CCG Pro | TTC Phe | TTA Leu | TTC Phe | CGC Arg | 96 |

|     |     |     |     |     |     |     |     |     |     |     |     |     |     |     |
|-----|-----|-----|-----|-----|-----|-----|-----|-----|-----|-----|-----|-----|-----|-----|
| Thr | Val | Tyr | Arg | Val | Arg | Leu | Leu | Pro | Asp | Ser | Pro | Phe | Leu | Phe | Arg |
|     |     |     | 20  |     |     |     |     | 25  |     |     |     |     | 30  |     |     |

| GCC | GGT | CAG | TAT | CTG | ATG | GTG | GTA | ATG | GAT | GAG | AGA | GAT | AAA | CGT | CCG | 144 |
|-----|-----|-----|-----|-----|-----|-----|-----|-----|-----|-----|-----|-----|-----|-----|-----|-----|
| Ala | Gly | Gln | Tyr | Leu | Met | Val | Val | Met | Asp | Glu | Arg | Asp | Lys | Arg | Pro |     |
|     |     | 35  |     |     |     |     | 40  |     |     |     |     | 45  |     |     |     |     |

| TTT | TCA | ATG | GCG | TCA | ACG | CCT | TCA | GAA | AAG | GAG | TTT | ATT | GAA | TTA | CAT | 192 |
| Phe | Ser | Met | Ala | Ser | Thr | Pro | Ser | Glu | Lys | Glu | Phe | Ile | Glu | Leu | His |     |
|     | 50  |     |     |     |     | 55  |     |     |     |     | 60  |     |     |     |     |     |

| ATT | GGT | GCT | TCT | GAA | CTG | AAT | TTG | TAT | GCA | ATG | GCT | GTG | ATG | GAT | AGA | 240 |
| Ile | Gly | Ala | Ser | Glu | Leu | Asn | Leu | Tyr | Ala | Met | Ala | Val | Met | Asp | Arg |     |
| 65  |     |     |     |     | 70  |     |     |     |     | 75  |     |     |     |     | 80  |     |

| ATT | CTG | GAT | CAG | AAA | GTG | ATC | AAT | ATT | GAT | ATC | CCT | CAT | GGC | AAA | GCT | 288 |
| Ile | Leu | Asp | Gln | Lys | Val | Ile | Asn | Ile | Asp | Ile | Pro | His | Gly | Lys | Ala |     |
|     |     |     |     | 85  |     |     |     |     | 90  |     |     |     |     | 95  |     |     |

| TGG | TTC | CGT | AAA | AGC | AGC | GCT | AAT | CCG | TTG | TTA | TTA | ATT | GCT | GGC | GGT | 336 |
| Trp | Phe | Arg | Lys | Ser | Ser | Ala | Asn | Pro | Leu | Leu | Leu | Ile | Ala | Gly | Gly |     |
|     |     |     | 100 |     |     |     |     | 105 |     |     |     |     | 110 |     |     |     |

| ACG | GGG | TTT | TCT | TAC | ACC | CGT | TCA | ATA | TTA | TTG | ACA | GCG | TTG | GAA | GAA | 384 |
| Thr | Gly | Phe | Ser | Tyr | Thr | Arg | Ser | Ile | Leu | Leu | Thr | Ala | Leu | Glu | Glu |     |
|     |     |     | 115 |     |     |     |     | 120 |     |     |     |     | 125 |     |     |     |

| CAA | CCA | AAA | CGT | CAT | ATC | TCT | ATG | TAT | TGG | GGG | GGC | AGA | GAA | TCA | CAA | 432 |
| Gln | Pro | Lys | Arg | His | Ile | Ser | Met | Tyr | Trp | Gly | Gly | Arg | Glu | Ser | Gln |     |
|     | 130 |     |     |     |     | 135 |     |     |     |     | 140 |     |     |     |     |     |

| CAT | TTA | TAT | GAT | CTT | GCT | GAA | TTA | CGG | TTA | CTT | ACA | GAA | CGC | TAT | CCT | 480 |
| His | Leu | Tyr | Asp | Leu | Ala | Glu | Leu | Arg | Leu | Leu | Thr | Glu | Arg | Tyr | Pro |     |
| 145 |     |     |     |     | 150 |     |     |     |     | 155 |     |     |     |     | 160 |     |

| AAT | TTG | AAG | GTT | ATT | CCA | GTT | GTT | GAA | CAG | TCA | GAT | AAT | GGT | TGG | TGT | 528 |
| Asn | Leu | Lys | Val | Ile | Pro | Val | Val | Glu | Gln | Ser | Asp | Asn | Gly | Trp | Cys |     |
|     |     |     |     | 165 |     |     |     |     | 170 |     |     |     |     | 175 |     |     |

| GGA | CGT | ACA | GGA | ACA | GTG | CTT | AAA | GCA | GTA | CTA | GAG | GAT | TTT | GGT | AGT | 576 |
| Gly | Arg | Thr | Gly | Thr | Val | Leu | Lys | Ala | Val | Leu | Glu | Asp | Phe | Gly | Ser |     |
|     |     |     | 180 |     |     |     |     | 185 |     |     |     |     | 190 |     |     |     |

| TTG | GCC | AAT | TAT | GAT | ATC | TAC | ATT | GCA | GGG | CGA | TTC | GAA | ATG | GCA | AAA | 624 |
| Leu | Ala | Asn | Tyr | Asp | Ile | Tyr | Ile | Ala | Gly | Arg | Phe | Glu | Met | Ala | Lys |     |
|     |     | 195 |     |     |     |     | 200 |     |     |     |     | 205 |     |     |     |     |

| ATT | GCT | CGC | GAG | CGC | TTT | TGT | AGT | GAG | CGT | GAT | GCT | TCT | GCT | GAC | AGC | 672 |
| Ile | Ala | Arg | Glu | Arg | Phe | Cys | Ser | Glu | Arg | Asp | Ala | Ser | Ala | Asp | Ser |     |
|     | 210 |     |     |     |     | 215 |     |     |     |     | 220 |     |     |     |     |     |

| ATG | TAT | GGT | GAT | GCT | TTC | GAA | TTC | ATT | TRR | 702 |
| Met | Tyr | Gly | Asp | Ala | Phe | Glu | Phe | Ile |     |     |
| 225 |     |     |     |     | 230 |     |     |     |     |     |

( 2 ) INFORMATION FOR SEQ ID NO:4:

( i ) SEQUENCE CHARACTERISTICS:
        ( A ) LENGTH: 1225 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 53..751

( x i ) SEQUENCE DESCRIPTION: SEQ ID NO:4:

GTCGACAAAA TCTGGGATGA ATTAGATATT TTAGGACCAT AAGAGGGAAC GC ATG   55
                                                                                                                              Met
                                                                                                                              1

| ACA | ACA | CTG | AGC | TGT | AAA | GTA | ACC | TCT | GTA | GAG | GCT | ATT | ACT | GAT | ACG | 103 |
| Thr | Thr | Leu | Ser | Cys | Lys | Val | Thr | Ser | Val | Glu | Ala | Ile | Thr | Asp | Thr |     |
|     |     |     | 5   |     |     |     |     | 10  |     |     |     |     | 15  |     |     |     |

| | | | | | | | | | | | | | | | | |
|---|---|---|---|---|---|---|---|---|---|---|---|---|---|---|---|---|
| GTT | TAT | CGG | GTA | CGG | TTG | CTT | CCC | GAT | TCT | CCG | TTC | TTA | TTC | CGC | GCC | 151 |
| Val | Tyr | Arg | Val | Arg | Leu | Leu | Pro | Asp | Ser | Pro | Phe | Leu | Phe | Arg | Ala | |
| | | 20 | | | | | 25 | | | | | 30 | | | | |
| GGT | CAG | TAT | CTG | ATG | GTG | GTA | ATG | GAT | GAG | AGA | GAT | AAA | CGT | CCG | TTT | 199 |
| Gly | Gln | Tyr | Leu | Met | Val | Val | Met | Asp | Glu | Arg | Asp | Lys | Arg | Pro | Phe | |
| | 35 | | | | | 40 | | | | | 45 | | | | | |
| TCA | ATG | GCG | TCA | ACG | CCT | TCA | GAA | AAG | GAG | TTT | ATT | GAA | TTA | CAT | ATT | 247 |
| Ser | Met | Ala | Ser | Thr | Pro | Ser | Glu | Lys | Glu | Phe | Ile | Glu | Leu | His | Ile | |
| 50 | | | | | 55 | | | | | 60 | | | | | 65 | |
| GGT | GCT | TCT | GAA | CTG | AAT | TTG | TAT | GCA | ATG | GCT | GTG | ATG | GAT | AGA | ATT | 295 |
| Gly | Ala | Ser | Glu | Leu | Asn | Leu | Tyr | Ala | Met | Ala | Val | Met | Asp | Arg | Ile | |
| | | | | 70 | | | | | 75 | | | | | 80 | | |
| CTG | GAT | CAG | AAA | GTG | ATC | AAT | ATT | GAT | ATC | CCT | CAT | GGC | AAA | GCT | TGG | 343 |
| Leu | Asp | Gln | Lys | Val | Ile | Asn | Ile | Asp | Ile | Pro | His | Gly | Lys | Ala | Trp | |
| | | | 85 | | | | | 90 | | | | | 95 | | | |
| TTC | CGT | AAA | AGC | AGC | GCT | AAT | CCG | TTA | TTA | ATT | GCT | GGC | GGT | ACG | | 391 |
| Phe | Arg | Lys | Ser | Ser | Ala | Asn | Pro | Leu | Leu | Leu | Ile | Ala | Gly | Gly | Thr | |
| | | 100 | | | | | 105 | | | | | 110 | | | | |
| GGG | TTT | TCT | TAC | ACC | CGT | TCA | ATA | TTA | TTG | ACA | GCG | TTG | GAA | GAA | CAA | 439 |
| Gly | Phe | Ser | Tyr | Thr | Arg | Ser | Ile | Leu | Leu | Thr | Ala | Leu | Glu | Glu | Gln | |
| | 115 | | | | | 120 | | | | | 125 | | | | | |
| CCA | AAA | CGT | CAT | ATC | TCT | ATG | TAT | TGG | GGG | GGC | AGA | GAA | TCA | CAA | CAT | 487 |
| Pro | Lys | Arg | His | Ile | Ser | Met | Tyr | Trp | Gly | Gly | Arg | Glu | Ser | Gln | His | |
| 130 | | | | | 135 | | | | | 140 | | | | | 145 | |
| TTA | TAT | GAT | CTT | GCT | GAA | TTA | CGG | TTA | CTT | ACA | GAA | CGC | TAT | CCT | AAT | 535 |
| Leu | Tyr | Asp | Leu | Ala | Glu | Leu | Arg | Leu | Leu | Thr | Glu | Arg | Tyr | Pro | Asn | |
| | | | | 150 | | | | | 155 | | | | | 160 | | |
| TTG | AAG | GTT | ATT | CCA | GTT | GTT | GAA | CAG | TCA | GAT | AAT | GGT | TGG | TGT | GGA | 583 |
| Leu | Lys | Val | Ile | Pro | Val | Val | Glu | Gln | Ser | Asp | Asn | Gly | Trp | Cys | Gly | |
| | | | 165 | | | | | 170 | | | | | 175 | | | |
| CGT | ACA | GGA | ACA | GTG | CTT | AAA | GCA | GTA | CTA | GAG | GAT | TTT | GGT | AGT | TTG | 631 |
| Arg | Thr | Gly | Thr | Val | Leu | Lys | Ala | Val | Leu | Glu | Asp | Phe | Gly | Ser | Leu | |
| | | 180 | | | | | 185 | | | | | 190 | | | | |
| GCC | AAT | TAT | GAT | ATC | TAC | ATT | GCA | GGG | CGA | TTC | GAA | ATG | GCA | AAA | ATT | 679 |
| Ala | Asn | Tyr | Asp | Ile | Tyr | Ile | Ala | Gly | Arg | Phe | Glu | Met | Ala | Lys | Ile | |
| | 195 | | | | | 200 | | | | | 205 | | | | | |
| GCT | CGC | GAG | CGC | TTT | TGT | AGT | GAG | CGT | GAT | GCT | TCT | GCT | GAC | AGC | ATG | 727 |
| Ala | Arg | Glu | Arg | Phe | Cys | Ser | Glu | Arg | Asp | Ala | Ser | Ala | Asp | Ser | Met | |
| 210 | | | | | 215 | | | | | 220 | | | | | 225 | |
| TAT | GGT | GAT | GCT | TTC | GAA | TTC | ATT | TRRAATAATA | AAAAACCCG | CCCCTGACAG | | | | | | 781 |
| Tyr | Gly | Asp | Ala | Phe | Glu | Phe | Ile | | | | | | | | | |
| | | | | 230 | | | | | | | | | | | | |

| | | | | |
|---|---|---|---|---|
| GCGGGAATTA | CGGCAACAAC | GACTCAGTTA | TAATAATTCT | TATATACCCG | TCATCTTTCA | 841 |
| AGTTGCCTCT | TTGTTGGCTG | CACTCACTCA | CCCCGGTTAC | ATAGTTTTCT | ATGCTCCTGG | 901 |
| GGATTCATTC | ACTTGCCGCC | GCGCTGCAAC | TCGAAATCTA | TTAGGTATAG | ATAAGTTCTT | 961 |
| AATCCATTCT | TTCTATAATG | GTGGCGATAC | CTTGGCCTAA | ACCGATACAC | ATGGTTGCTA | 1021 |
| GGCCAAACTG | AACATCGCGG | CGTTCCATTA | AGTTCAACAA | CGTTGTTGTG | ATGCGAGCGC | 1081 |
| CTGAGCAGCC | TAAAGGATGA | CCCAGAGCAA | TTGCGCCACC | ATTCAGGTTA | ACTTTGTCAT | 1141 |
| CCATACTATC | CAGCAAATTC | AGACTTTCAG | GCAGGCAAGT | GACTGAGCAG | CAAATGCTTC | 1201 |
| GTTTAGTTCA | ATCACGCCGA | TATC | | | | 1225 |

( 2 ) INFORMATION FOR SEQ ID NO:5:

( i ) SEQUENCE CHARACTERISTICS:
        ( A ) LENGTH: 233 amino acids
        ( B ) TYPE: amino acid
        ( C ) STRANDEDNESS: single
        ( D ) TOPOLOGY: unknown ( i i ) MOLECULE TYPE: protein ( x i ) SEQUENCE DESCRIPTION: SEQ ID NO:5:

| Met | Thr | Thr | Leu | Ser | Cys | Lys | Val | Thr | Ser | Val | Glu | Ala | Ile | Thr | Asp |
| 1 | | | | 5 | | | | | 10 | | | | | 15 | |

| Thr | Val | Tyr | Arg | Val | Arg | Leu | Leu | Pro | Asp | Ser | Pro | Phe | Leu | Phe | Arg |
| | | | 20 | | | | | 25 | | | | | 30 | | |

| Ala | Gly | Gln | Tyr | Leu | Met | Val | Val | Met | Asp | Glu | Arg | Asp | Lys | Arg | Pro |
| | | 35 | | | | | 40 | | | | | 45 | | | |

| Phe | Ser | Met | Ala | Ser | Thr | Pro | Ser | Glu | Lys | Glu | Phe | Ile | Glu | Leu | His |
| | 50 | | | | | 55 | | | | | | 60 | | | |

| Ile | Gly | Ala | Ser | Glu | Leu | Asn | Leu | Tyr | Ala | Met | Ala | Val | Met | Asp | Arg |
| 65 | | | | | 70 | | | | | 75 | | | | | 80 |

| Ile | Leu | Asp | Gln | Lys | Val | Ile | Asn | Ile | Asp | Ile | Pro | His | Gly | Lys | Ala |
| | | | | 85 | | | | | 90 | | | | | 95 | |

| Trp | Phe | Arg | Lys | Ser | Ser | Ala | Asn | Pro | Leu | Leu | Leu | Ile | Ala | Gly | Gly |
| | | | 100 | | | | | 105 | | | | | 110 | | |

| Thr | Gly | Phe | Ser | Tyr | Thr | Arg | Ser | Ile | Leu | Leu | Thr | Ala | Leu | Glu | Glu |
| | | 115 | | | | | 120 | | | | | 125 | | | |

| Gln | Pro | Lys | Arg | His | Ile | Ser | Met | Tyr | Trp | Gly | Gly | Arg | Glu | Ser | Gln |
| | 130 | | | | | 135 | | | | | 140 | | | | |

| His | Leu | Tyr | Asp | Leu | Ala | Glu | Leu | Arg | Leu | Leu | Thr | Glu | Arg | Tyr | Pro |
| 145 | | | | | 150 | | | | | 155 | | | | | 160 |

| Asn | Leu | Lys | Val | Ile | Pro | Val | Val | Glu | Gln | Ser | Asp | Asn | Gly | Trp | Cys |
| | | | | 165 | | | | | 170 | | | | | 175 | |

| Gly | Arg | Thr | Gly | Thr | Val | Leu | Lys | Ala | Val | Leu | Glu | Asp | Phe | Gly | Ser |
| | | | 180 | | | | | 185 | | | | | 190 | | |

| Leu | Ala | Asn | Tyr | Asp | Ile | Tyr | Ile | Ala | Gly | Arg | Phe | Glu | Met | Ala | Lys |
| | | 195 | | | | | 200 | | | | | 205 | | | |

| Ile | Ala | Arg | Glu | Arg | Phe | Cys | Ser | Glu | Arg | Asp | Ala | Ser | Ala | Asp | Ser |
| | 210 | | | | | 215 | | | | | 220 | | | | |

| Met | Tyr | Gly | Asp | Ala | Phe | Glu | Phe | Ile |
| 225 | | | | | 230 | | | |

( 2 ) INFORMATION FOR SEQ ID NO:6:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:6:

ATGACAACCT TAAGCTGTAA AGTG     24

( 2 ) INFORMATION FOR SEQ ID NO:7:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:7:

TCAGATAAAT GCAAACGCAT CGCC     24

FLAVIN REDUCTASE GENE

This application is a continuation of patent application Ser. No. 08/250,855, filed May 27, 1994 now abandoned.

TECHNICAL FIELD OF THE INVENTION

The present invention provides nucleic acids coding for the flavin reductase of a luminescent bacterium, *Xenorhabdus luminescens*. This invention also relates to vectors comprising such nucleic acids and host cells into which these vectors have been introduced. The invention further relates to recombinant methods for the production of substantially purified recombinant flavin reductase wherein the protein is expressed in a host cell of the present invention, as well as to recombinantly produced flavin reductase produced in accordance with such methods.

BACKGROUND OF THE INVENTION

Luciferase is an enzyme derived from a luminescent bacterium. The enzyme catalyzes a reaction that involves a reduced flavin mononucleotide (hereinafter referred to as "$FMNH_2$") and a long chain fatty aldehyde as substrates in the presence of oxygen. An oxidized flavin mononucleotide (hereinafter referred to "FMN") and a long chain fatty acid are produced thereby along with the emission of a blue color light.

In the cell, the substrate $FMNH_2$ used in this reaction is supplied by the reducing action of nicotinamide adenine dinucleotide:flavin mononucleotide (NADH:FMN) reductase and nicotinamide adenine dinucleotide phosphate:flavin mononucleotide (NADPH:FMN) reductase; and the long chain fatty aldehyde is supplied from a fatty acid reductase complex.

Recently, Spyrou et al. (*J. Bacteriol.*, 173, 3673–3679 (1991)) isolated a flavin reductase gene from *Escherichia coli* and elucidated its primary structure.

The present inventors have also isolated a FMN reductase gene, that of the luminescent bacterium, *Vibrio fischeri*. The inventors have determined its nucleotide sequence, and further have succeeded in expressing the gene in *E. coli* (Japanese Patent Application No. Hei 03-351,717). However, isolation of the flavin reductase gene from the luminescent bacterium *Xenorhabdus luminescens* and its expression in *E. coli* has not yet been reported.

$FMNH_2$ is easily and instantaneously autoxidized in air and converted into FMN. In order to have the luminescent ability of bacterial luciferase displayed to the maximum, it is necessary to continuously supply the $FMNH_2$ as a substrate. FMN reductase is most important in order to achieve this object.

As described above, this enzyme conjugates with the bacterial luciferase and catalyzes the reaction of converting FMN as the product of the luciferase reaction into $FMNH_2$; thus, luciferase and FMN reductase are made coexistent in the reaction system; and as a result, it is possible to retain the luminescent reaction. Namely, since the bacterial luciferase is many times subjected to turnover, the bacterium retains the luminescence as far as the long chain aldehyde in a large excess is existent in the reaction system.

As described above, FMN reductase is indispensable for making the most of the bacterial luciferase, and by obtaining the gene, it is possible to prepare FMN reductase enzyme in large quantities.

In view of this, it is an object of the present invention to provide nucleic acids coding for flavin reductase of a luminescent bacterium, *X. luminescens*. It is another object of the invention to provide vectors comprising such nucleic acids, and host cells into which these vectors have been introduced. Yet another object of the invention is to provide recombinant methods for the production of substantially purified recombinant flavin reductase, wherein the protein is expressed in a host cell of the present invention. A further object of the invention is to provide recombinant flavin reductase produced in accordance with such methods.

These and other objects and advantages of the invention, as well as additional inventive features, will be more readily apparent from the description of the invention provided herein.

BRIEF SUMMARY OF THE INVENTION

The present invention provides nucleic acids coding for the flavin reductase of a luminescent bacterium, *Xenorhabdus luminescens*. Also provided are vectors comprising such nucleic acids and host cells into which these vectors have been introduced. The invention further provides recombinant methods for the production of substantially purified recombinant flavin reductase, wherein the protein is expressed in a host cell of the present invention. Moreover, the present invention provides recombinant flavin reductase produced in accordance with such methods.

BRIEF DESCRIPTION OF THE DRAWINGS

FIG. 1 illustrates the amino acid sequence of the flavin reductase gene of *Escherichia coli* and synthesized oligonucleotide primers corresponding to the amino (FRE 1; ID Seq. No:6) and carboxy (FRE 2; ID Seq. No:7) termini.

FIG. 3 illustrates the construction of the expression vector pXFR1 containing the flavin reductase gene of *X. luminescens*. The white boxes correspond to the coding region of the flavin reductase gene. The dotted lines correspond to portions of the pUC vector.

Figure 2:
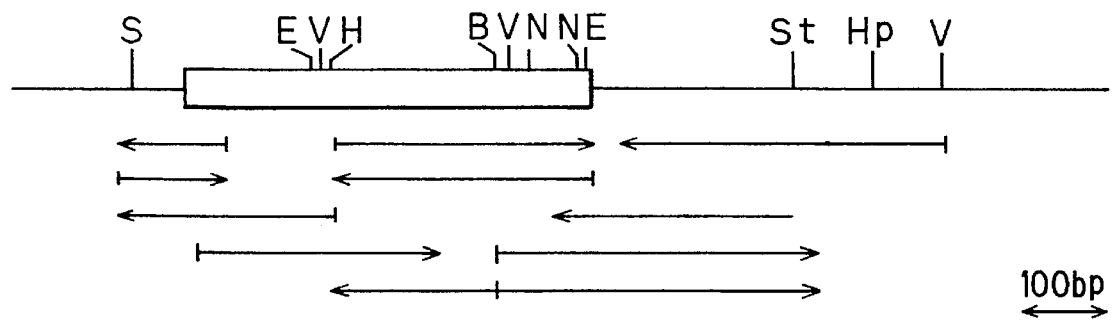
FIG. 2 illustrates a restriction map of the flavin reductase gene of *Xenorhabdus luminescens*, and the strategy employed for sequencing this gene. The arrows indicate the direction in which the nucleotide sequence was determined. The box corresponds to the structural portion of the gene.

The black boxes correspond to the promotor of lactose operon of *E. coli*.

DETAILED DESCRIPTION OF THE PREFERRED EMBODIMENTS

The nucleic acids of the present invention have been isolated for the first time, and code for a protein having the FMN reduction activity (or more generally, flavin reduction activity, or FMN or flavin reductase; such terms will be used interchangeably) of the luminescent bacterium, *Xenorhabdus luminescens* (ATCC 29999). The nucleic acids comprise substantially purified genomic DNA. By transfer of vectors comprised of these nucleic acids into a suitable host, for example, *Escherichia coli*, it is possible to produce an organism or microorganism expressing a protein having the FMN reduction activity of a luminescent bacterium, in a large quantity. Furthermore, it is possible to prepare the reductase in a large quantity from the host, as described herein.

Accordingly, the present invention provides substantially purified nucleic acid sequences coding for the flavin reductase of *X. luminescens*. The flavin reductase gene of the present invention is 702 base pairs in length and comprises the sequence of SEQ ID NO:1. Thus the present invention provides a substantially purified nucleic acid comprising the nucleic acid sequence of SEQ ID NO:1. With respect to SEQ ID NO:1, different codons are possible for particular amino acids as follows: YTN can code for leu (TTA, CTA, TTG, CTG, CTC or CTT); NGN can code for arg (CGC, CGT, AGA, CGG, CGA or AGG), ser (AGC or AGT), gly (GGA, GGC, GGG) or ala (GCT); and NNN can code for ser (TCA, TCT, AGC, AGT, TCG or TCC).

The sequence variations in SEQ ID NO:1 may be artifactual (e.g., resulting from an inability to "read" the sequence at various points during sequencing), or may have resulted from natural host variations or polymorphisms. Accordingly, SEQ ID NO:2 and SEQ ID NO:3 set forth more preferred nucleic acid sequences. SEQ ID NO:4 sets forth sequences coding for the flavin reductase of *X. luminescens*, as well as sequences flanking the flavin reductase gene on both 5' and 3' ends.

Thus, the present invention sets forth a substantially purified nucleic acid comprising the nucleic acid sequence of SEQ ID NO:2. With respect to SEQ ID NO:2, different codons for leucine, arginine and serine are possible as follows: YTN can code for leu (TTA, CTA, TTG, CTG, CTC or CTT); NGN can code for arg (CGC, CGT, AGA, CGG, CGA or AGG); and NNN can code for ser (TCA, TCT, AGC, AGT, TCG or TCC).

The present invention also sets forth a substantially purified nucleic acid comprising the nucleic acid sequence of SEQ ID NO:3. With respect to SEQ ID NO:3, codons for leucine, arginine and serine are as specified in the sequence.

Similarly, the present invention sets forth a substantially purified nucleic acid comprising the nucleic acid sequence of SEQ ID NO:4. The sequence length of SEQ ID NO:4 is 1225 base pairs. The coding region of the flavin reductase gene is located between nucleotide positions 53 and 751 of the genomic DNA fragment, as set forth in SEQ ID NO:4. This sequence also displays DNA flanking the gene on its 5' and 3' ends.

The nucleic acids of SEQ ID NO:1, SEQ ID NO:2, SEQ ID NO:3 and SEQ ID NO:4 encode a protein of a molecular weight of 26439 daltons, consisting of 233 amino acids, as set forth in SEQ ID NO:5. SEQ ID NO:5 was determined from the nucleotide sequence of SEQ ID NO:1, SEQ ID NO:3 and SEQ ID NO:4. Accordingly, the present invention provides a substantially purified protein comprising the amino acid sequence of SEQ ID NO:5. This protein has a flavin-reducing activity, for example, a FMN reducing activity.

The present invention also provides recombinant vectors. For instance, the present invention provides: a vector which comprises a nucleic acid comprising the nucleic acid sequence of SEQ ID NO:1 and a functional equivalent thereto; a vector which comprises a nucleic acid comprising the nucleic acid sequence of SEQ ID NO:2 and a functional equivalent thereto; a vector which comprises a nucleic acid comprising the nucleic acid sequence of SEQ ID NO:3 and a functional equivalent thereto; a vector which comprises a nucleic acid comprising the nucleic acid sequence of SEQ ID NO:4 and a functional equivalent thereto.

The "functional equivalent" refers to a DNA fragment which is usable according to substantially the same method in order to obtain substantially the same results, in the production of an enzyme having the FMN-reducing activity of a luminescent bacterium, by means of a suitable host.

Namely, the functional equivalent refers to a DNA fragment capable of coding a protein having the same amino acid sequence even when the nucleotide sequence is different, or a DNA fragment capable of coding a protein having a FMN-reducing activity even when there occurs a certain extent of difference of an amino acid sequence accompanying a certain extent of difference of the nucleotide sequence. The functional equivalent also refers to a nucleotide sequence of SEQ ID NO:1 or a nucleotide sequence of SEQ ID NO:1 mutated by side-directed mutagenesis.

The present invention further provides: a vector which comprises a nucleic acid comprising the nucleic acid sequence of SEQ ID NO:1; a vector which comprises a nucleic acid comprising the nucleic acid sequence of SEQ ID NO:2; a vector which comprises a nucleic acid comprising the nucleic acid sequence of SEQ ID NO:3; a vector which comprises a nucleic acid comprising the nucleic acid sequence of SEQ ID NO:4.

A "functional equivalent" also may be used with respect to a construct obtained by inserting a DNA fragment having the nucleotide sequence into a plasmid vector. As such, a vector, such as pUC (Yanish-Perron et al., *Gene*, 33, 110–115 (1985)) or pIN III (Masui et al., in *Experimental Manipulation of Gene Expression* (ed. M. Inouye, Academic Press (1983), p. 15) may be employed, as may other vectors as have been described, and are known to those skilled in the art. Such vectors may be single or double stranded, linear or circular, may possess different host ranges, and may even allow the subcloned DNA to be placed under the control of a controlling element, such as a promoter, contained within the vector. It is not strictly necessary that the vector be capable of autonomous replication in a host, but preferably, the vector should allow transmission of a subcloned gene, and possibly also, expression of the gene.

Accordingly, the present invention provides a host cell containing a vector which comprises: a nucleic acid comprising the nucleic acid sequence of SEQ ID NO:1 and a functional equivalent thereto; a nucleic acid comprising the nucleic acid sequence of SEQ ID NO:2 and a functional equivalent thereto; a nucleic acid comprising the nucleic acid sequence of SEQ ID NO:3 and a functional equivalent thereto; a nucleic acid comprising the nucleic acid sequence of SEQ ID NO:4 and a functional equivalent thereto.

The present invention similarly provides a host cell containing a vector which comprises: a nucleic acid comprising the nucleic acid sequence of SEQ ID NO:1; a nucleic acid comprising the nucleic acid sequence of SEQ ID NO:2; a nucleic acid comprising the nucleic acid sequence of SEQ ID NO:3; a nucleic acid comprising the nucleic acid sequence of SEQ ID NO:4.

FIG. 3 illustrates the construction steps of the recombinant vector (i.e., in this case an expression vector) according to the present invention. Namely, from the recombinant phage DNA λXS$_{40}$ containing the reductase gene, a Sal I fragment of about 4 Kb of the gene was excised and inserted into the Sal I cleavage site of pUC13, to yield the recombinant plasmid pXS$_{14}$. The pXS$_{14}$ plasmid DNA was then digested with Hpa I and Sma I, and religated. This resulted in the elimination from the plasmid of a fragment of about 3 kb. The resultant expression vector, pXFR1, contains the flavin reductase gene has under the control of the lac promotor, allowing controlled expression of this flavin reductase gene.

The bacterium of the present invention contains a recombinant vector DNA containing a nucleotide sequence expressed by SEQ ID NO:1. The bacterium of the present invention is characterized by producing a protein having a flavin-reducing activity.

The present invention also provides a method of producing a protein which comprises the amino acid sequence of SEQ ID NO:5. Briefly, according to this method, a vector comprising a nucleic acid which codes for said protein (e.g., a nucleic acid comprising the nucleic acid sequence of SEQ ID NO:1, SEQ ID NO:2, SEQ ID NO:3 or SEQ ID NO:4) is introduced in a host cell, the host cell is grown under conditions wherein the protein is produced, and the protein is isolated from the host.

More particularly as set forth herein (and as described in the art and well known to one of ordinary skill in the art) the process for producing the enzyme of the present invention consists of cultivating a bacterium modified by a recombinant vector (i.e., preferably an expression vector) containing a subcloned DNA comprised of the nucleotide sequence of SEQ ID NO:1, to produce a protein comprising the amino acid sequence of SEQ ID NO:5. Examples of the bacteria which may be employed are *E. coli, Bacillus subtilis* and the like. Examples of the medium which may be employed for growth are LB medium, YT medium and the like. This medium may be supplemented with such components as are necessary to allow or increase expression of the subcloned gene or gene fragment contained in the vector.

The isolation of the gene and its identification as well as importance in the present invention will be described by means of the Examples which follow. These Examples serve only to illustrate further the present invention and are not to be construed as limiting its scope in any way.

EXAMPLE 1

Isolation of the *E. coli* flavin reductase gene (fre) and Southern genomic analysis of various luminescent bacteria.

*E. coli* strain C 600 was grown overnight with shaking in LB medium at 37° C. The cells were harvested by centrifugation at 10,000 rpm, and the bacterial pellet was resuspended in Tris HCl.EDTA buffer solution (hereinafter referred to as "TE buffer solution").

The resulting suspension was treated with lysozyme at 37° C. for one hour, followed by addition of sodium dodecyl sulfate (hereinafter referred to as "SDS"), and proteinase K digestion. The solution was extracted with phenol three times, precipitated with ethanol, dried and dissolved in the TE buffer solution. The solution was then again subjected to proteinase K digestion, was extracted with phenol three times and precipitated with ethanol to recover genomic DNA.

The coding region of a flavin reductase gene (fre) of *E. coli* (clarified by Spyrou et al., supra) was amplified with synthesized oligonucleotide primer FRE 1 (SEQ ID NO:6) and FRE 2 (SEQ ID NO:7) shown in FIG. 1, according to the PCR method of Saiki et al., *Science* 239, 487 (1988). The DNA fragment was then inserted into the Hind II-cleavage site of the pUC8 plasmid (Hanna et al., *Gene*, 30, 247 (1984)).

The resultant plasmid was confirmed to contain the *E. coli* fre gene, according the method of Hattori et al. (*Anal. Biochem.*, 152, 232 (1986). From the plasmid, the fre gene-containing portion was excised using the restriction enzymes Hind III and Eco RI. This fragment was used as a probe for Southern analysis of genomic DNA from various luminescent bacteria. The $^{32}$P-labelling of the fre probe DNA was carried out according to the random priming method of Feinberg et al., *Anal. Biochem*, 132, 6 (1983).

The luminescent bacteria *Alteromonas hanedai, Vibrio harveyi, Vibrio fischeri* and *Vibrio orientalis* were grown overnight with shaking in Photobacterium medium at 26° C. The luminescent bacterium *X. luminescens* was grown overnight with shaking in LB medium at 37° C. The genomic DNA of the respective luminescent bacteria was isolated in the same manner described above.

The respective genome DNAs were completely digested with Eco RI or Hind III, followed by agarose gel electrophoresis of the digested DNA. Southern analysis was carried out according to Sambrook et al., *Molecular Cloning: A Laboratory Manual* (2d ed., Cold Spring Harbor Laboratory, Cold Spring Harbor, N.Y. (1989)).

The filter used for hybridization was dried with air, followed by irradiating it with ultraviolet ray (UV) to fix the DNA, placing it in a hybridization solution (20 ml) comprised of: 6× SET buffer solution, prepared from a 20× SET buffer solution that contained: 3M NaCl, 0.6M Tris-Hcl (pH 8.0) and 0.04M EDTA; 10× Denhardt's solution, which is a solution of 2% each bovine sperm albumin, polyvinyl pyrrolidone and Ficoll; 0.1% SDS; and 50 µg/ml salmon sperm DNA (thermally modified). The hybridization solution was kept at 68° C. for one hour, further replacing the solution, keeping the temperature for one hour, adding a probe of $^{32}$P-labeled *E. coli* fre, subjecting the mixture to hybridization at 50° C. for one night, discarding the solution, washing the filter with 6× SET buffer solution, shaking 6× SET buffer solution at 55° C. for 20 minutes, repeating the procedure twice, drying with air and subjecting to autoradiography.

As a result, a band of 5.0 kilobase (Kb) in the case of Eco RI and a band of 4.0 Kb in the case of Hind III were detected in only *X. luminescens*.

EXAMPLE 2

Preparation of a library of *X. luminescens* genes in *E. coli*.

A luminescent bacterium, *X. luminescens* (ATCC 29999), was cultivated on LB medium at 37° C. overnight under shaking, followed by collecting bacteria according to centrifugal separation 10,000 rpm, suspending the bacterial cells in a TE buffer solution, treating the resulting suspension with lysozyme at 37° C. for one hour, adding SDS, subjecting the mixture to proteinase K treatment at 50° C. for 3 hours, repeating phenol treatment three times, precipitating with ethanol, drying, dissolving in TE buffer solution, again subjecting to proteinase K treatment, treating with phenol three times and precipitating with ethanol, to recover genome DNA.

About 50 µg of the genomic DNA was digested with 100 units of Hind III at 37° C. for 120 minutes. The digestion reaction was terminated by adding EDTA (ethylenediaminetetra-acetic acid), following which the DNA was precipitated with ethanol and recovered by centrifugation.

The recovered digested DNA was dissolved in a small quantity of TE buffer solution, and was subjected to agarose gel electrophoresis. A DNA size-fraction in the vicinity of 4 Kb was recovered using DE 81 paper, and was eluted from the paper with 1M NaCl, extracted with phenol three times, precipitated with ethanol, and dissolved in TE buffer solution at a final concentration of about 200 ng/µl.

The DNA of the above fraction was ligated overnight at 16° C. to pUC18 plasmid DNA which had been digested with Hind III and treated with an alkaline phosphatase (an enzyme which catalyzes removal of phosphoric acid at the 5' terminus of DNA), with a T4 DNA ligase (an enzyme connecting DNA chains to each other or connecting DNA to 3' OH and 5' phosphate terminuses of RNA so as to form phosphodiester bonds). The connected reaction solution was transformed into JM 109 *E. coli* and the resulting transformants constituted a gene library.

EXAMPLE 3

Isolation of the 3' end of the *X. luminescens* flavin reductase gene.

The gene library prepared in Example 2 was titered, followed by scattering the gene library on a nitrocellulose filter so as to give 200 colonies per one plate, cultivating at 37° C. overnight, and taking two sheets of replica per each of the respective filters. One set of two sheets of replica filters was cultivated at 37° C. and used for hybridization. The filter was air dried, followed by irradiating it with ultraviolet rays to fix the DNA, placing it in 20 ml of a hybridization solution, 6× SET buffer solution, 10× Denhardt's solution, 0.1% SDS, and 50 µg/ml salmon sperm DNA (thermally degenerated) and keeping the temperature at 68° C. for one hour.

Further, the solution was replaced, followed by keeping the temperature for one hour, adding the probe of $^{32}$P-labeled *E. coli* fre, hybridizing at 50° C. overnight, discarding the solution, washing the filter with a 6× SET buffer solution, shaking the 6× SET buffer solution at 55° C. for 20 minutes, twice repeating the procedure, drying with air, subjecting to autoradiography, overlaying the filter on the developed x-ray film, and photographing the site of the ink marker on the film. One colony (clone) wherein the signals were identified to overlap on two films made from one plate, was obtained from 100 transformants. This colony was named pXH3.

The pXH3-inserted DNA had the same size as 4.0 Kb obtained according to Southern analysis in Example 1. pXH3 plasmid DNA was subjected to Southern analysis, using *E. coli* fre as a probe and using various kinds of 6 nucleotides-recognizing restriction enzymes, to determine the hybridized region. The nucleotide sequence in the vicinity thereof was determined according to the dideoxy method of Hattori et al., *Anal. Biochem.*, 132, 232 (1986).

As a result, it was found that the sequence contained a portion corresponding to 3' side of the coding region of *E. coli* fre. This pXH3 was deficient of the coding region on 5' side; hence again in order to isolate a clone having a complete chain length, it was intended to newly prepare a gene library by partial decomposition with Sau 3AI.

EXAMPLE 4

Preparation of λ phage gene library of luminescent bacterium.

A luminescent bacterium, *X. luminescens* (ATCC 29999), was cultivated on LB medium at 37° overnight under shaking, followed by subjecting the culture to centrifugal separation at 10,000 rpm to collect the bacterial cells, suspending the cells in TE buffer solution, subjecting the suspension to lysozyme treatment at 37° C. for one hour, adding SDS, subjecting the mixture to proteinase K treatment, carrying out phenol treatment three times, precipitating with ethanol, drying, dissolving in TE buffer solution, again carrying out proteinase K treatment, carrying out phenol treatment three times and precipitating with ethanol to recover genome DNA.

This genome DNA (50 µg) was reacted with a restriction enzyme, Sau 3AI (10 units) at 37°C., followed by partly taking out the reaction substance at the respective reaction times of 5, 10, 20, 30, 45, 60, 90 and 120 minutes, adding EDTA (ethylenediamine tetracetate) to terminate the reaction, subjecting the respective parts to agarose gel electrophoresis to confirm the extent of the partial decomposition of the genome DNA, combining the reaction solutions at the respective times into one solution, precipitating with ethanol and recovering the resulting precipitate.

The precipitate was dissolved in a small quantity of TE buffer solution, followed by subjecting the solution to agarose gel electrophoresis, to recover fractions of 9 to 23 Kb according to electrically dissolving-out operations, electrophoretically dissolving out the above DNA of 9 to 23 Kbs fractions from the agarose gel containing the fractions of 9 to 23 Kbs into a dialytic tube, subjecting the DNA to phenol treatment three times, precipitating with ethanol, dissolving the precipitate in a TE buffer solution so as to give about 200 ng/µl, and connecting the above DNA of 9 to 23 Kbs to EMBL3 phage obtained with a restriction enzyme, Bam HI, in advance and treating with an alkaline phosphate (an enzyme catalyzing removal of phosphoric acid at 5' terminus of DNA), with T4 DNA ligase (an enzyme connecting DNA chains to each other or connecting DNA to 3' OH and 5' P terminuses of RNA so as to form phosphodiester bands) at 16° C. overnight.

The connected reaction solution was mixed with a packaging extraction solution, followed by reaction at 22° C. for 2 hours to prepare recombinant phages. These phages constituted a gene library.

EXAMPLE 5

Isolation of the full length *X. luminescens* flavin reductase gene.

The gene library prepared in Example 4 was titered, followed by scattering so that 10,000 phages per one plate could form plaques, cultivating at 37° C. overnight, allowing the culture to stand at 4° C. for 2 hours, and transferring the phages onto each two of the respective plates with a nylon membrane filter.

The filter was denatured, neutralized and irradiated with ultraviolet rays. Thereafter, in the same manner as in Example 3, hybridization was carried out at 68° C. for one hour and at 50° C. overnight, followed by autoradiography and isolation of one positive clone. This was named λXS40.

The phage DNA of λXS40 was digested with Sal I, followed by treating the digested substance at 70° C. for 10 minutes, precipitating with ethanol, dissolving the resulting substance in a small quantity of TE, connecting it to the digested substance of pUC18 with Sal I with T4 DNA ligase, and transforming the DNA solution into *E coli* JM 109 strain.

A plasmid DNA was prepared from the transformed strain, and using the pXH3-inserted DNA as a probe, the digested substance with Sal I was subjected to Southern analysis. As a result, a band of a fragment having 4.0 Kb was detected. The plasmid containing the fragment of 4.0 Kb was named pXS14.

Using a synthesized oligonucleotide primer (20 mer) prepared using the plasmid of pXS14 as a template, based upon the nucleotide sequence of pXH3, the nucleotide sequence of pXS14 was determined according to the dideoxy method of Hattori et al., supra.

Further a synthesized primer was newly prepared based upon the nucleotide sequence, and its nucleotide sequence was determined in the same manner. FIG. 2 illustrates the restriction map and the strategy of the sequence determination of pXS14.

The nucleotide sequence of the full length *X. luminescens* flavin reductase gene determined from pXH3 and pXS14 is as illustrated in SEQ ID NO:4, and it has a length of 1225 bp and is regarded as coding a protein consisting of 233 amino acids of nucleotide numbers from 53 to 751 and having a molecular weight of 26,439 daltons. The coding region had a homology of 67.0% on the nucleotide level and that of 73.0% on the level of amino acid, as compared with the fre gene of *E. coli*.

EXAMPLE 6

Construction of an expression vector containing the *X. luminescens* flavin reductase gene and transformation into *E. coli*.

An expression vector containing the *X. luminescens* flavin reductase gene was constructed as set forth in FIG. 3. The DNA of the recombinant plasmid pXS14 was digested with Hpa I and Sma I, followed by deactivating the respective enzymes, carrying out connecting reaction with T4 DNA ligase, transforming a portion of the reaction solution in *E. coli* D1210 strain, preparing a plasmid DNA from the transformant, and choosing an insert DNA having about 1 Kb.

The plasmid was named pXFR1. This pXFR1 was in the form wherein the flavin reductase gene was arranged under rule of the promotor of lactose operon (lac), and was constructed so as to express the flavin reductase.

EXAMPLE 7

Isolation of recombinant flavin reductase and measurement of its activity.

The solution (0.25 ml) obtained by cultivating the transformant overnight was inoculated into LB liquid medium (10 ml) containing ampicillin, followed by cultivating at 37° C. for 2 hours with shaking, adding isopropyl-β-D(−)-thiogalactopyranoside (abbreviated to IPTG) so as to give a final concentration of 1 mM and cultivating the mixture for 3 hours.

A culture solution (3.0 ml) obtained by the above IPTG-induced treatment was subjected to centrifugal separation at 10,000 rpm, followed by removing the supernatant, suspending the bacterial cells in a buffer solution (0.75 ml) and 50 mM potassium phosphate, 1 mM dithiothreitol, breaking the cell suspension by ultrasonification, and subjecting to centrifugal separation at 12,000 rpm at 4° C. for 30 minutes. The resulting supernatant was made a cell extraction liquid.

The enzyme reduction activity of this cell extraction liquid was measured. The results are shown in Table 1.

TABLE 1

| | Plasmid/ | Activity of flavin reductase (nmol/min/mg protein) | | |
|---|---|---|---|---|
| | Host | FMN | FAD | Riboflavin |
| NADH | pXFR1/D1210 | 116 | 55 | 124 |
| | pUC13/D1210 | 27 | 41 | 29 |
| NADPH | pXFR1/D1210 | 63 | 6 | 302 |
| | pUC13/D1210 | 4 | 6 | 19 |

The flavin reductase activity was determined according to the method of Jablonski et al. (*Biochemistry*, 16, 2932 (1977)). The quantity of protein was determined using a kit for protein analysis made by Bio-Rad Co., Ltd., according to the pigment-binding method of Bradford (*Anal. Biochem.*, 72, 248–254 (1976)).

As seen from the results of Table 1, FMN of pXFR1 or flavin reducing activity exhibited values higher by one order than those of plasmid vector pUC13. It was confirmed that this gene coded the flavin reductase.

Due to the above function, the reductase amplifies the luminescent reaction of the bacterial luciferase, and is applicable to many measurement methods and useful, for example, as a diagnostic reagent or test reagent.

All of the references cited herein, as well as the priority document JP 151076/1993, are hereby incorporated in their entireties by reference.

While this invention has been described with an emphasis upon preferred embodiments, it will be obvious to those of ordinary skill in the art that variations in the preferred nucleic acids coding for the *X. luminescens* flavin reductase, the vectors containing the preferred nucleic acids, the amino acid sequences of the flavin reductase, and the method of producing the flavin reductase may be realized, and that it is intended that the invention may be practiced otherwise than as specifically described herein. Accordingly, this invention includes all modifications encompassed within the spirit and scope of the invention as defined by the following claims.

What is claim is:

1. A substantially purified nucleic acid comprising the nucleic acid sequence of SEQ ID NO:1.
2. A substantially purified nucleic acid comprising the nucleic acid sequence of SEQ ID NO:2.
3. A substantially purified nucleic acid comprising the nucleic acid sequence of SEQ ID NO:3.
4. A substantially purified nucleic acid comprising the nucleic acid sequence of SEQ ID NO:4.
5. A vector which comprises a nucleic acid of claim 1.
6. A vector which comprises a nucleic acid of claim 2.
7. A vector which comprises a nucleic acid of claim 3.
8. A vector which comprises a nucleic acid of claim 4.
9. A host cell containing the vector of claim 5.
10. A host cell containing the vector of claim 6.
11. A host cell containing the vector of claim 7.
12. A host cell containing the vector of claim 8.
13. A method of producing a protein which comprises the amino acid sequence of SEQ ID NO:5, wherein:
    (a) a vector comprising a nucleic acid of claim 1 is introduced in a host cell,
    (b) the host cell is grown under conditions wherein said protein is produced, and
    (c) said protein is isolated from said host cell.
14. A method of producing a protein which comprises the amino acid sequence of SEQ ID NO:5, wherein:
    (a) a vector comprising a nucleic acid of claim 2 is introduced in a host cell,
    (b) the host cell is grown under conditions wherein said protein is produced, and
    (c) said protein is isolated from said host cell.
15. A method of producing a protein which comprises the amino acid sequence of SEQ ID NO:5, wherein:
    (a) a vector comprising a nucleic acid of claim 3 is introduced in a host cell,
    (b) the host cell is grown under conditions wherein said protein is produced, and
    (c) said protein is isolated from said host cell.
16. A method of producing a protein which comprises the amino acid sequence of SEQ ID NO:5, wherein:
    (a) a vector comprising a nucleic acid of claim 4 is introduced in a host cell,
    (b) the host cell is grown under conditions wherein said protein is produced, and
    (c) said protein is isolated from said host cell.

* * * * *